United States Patent [19]
Thenappan et al.

[11] Patent Number: 5,856,594
[45] Date of Patent: Jan. 5, 1999

[54] PROCESS FOR THE PREPARATION OF 1,1,2,2,3-PENTAFLUOROPROPANE

[75] Inventors: Alagappan Thenappan, Cheektowaga; Michael Van Der Puy, Amherst; David Nalewajek, West Seneca, all of N.Y.

[73] Assignee: AlliedSignal Inc., Morristown, N.J.

[21] Appl. No.: 728,537

[22] Filed: Oct. 9, 1996

Related U.S. Application Data

[63] Continuation of Ser. No. 418,318, Apr. 7, 1995, abandoned.

[51] Int. Cl.$^6$ ..................................................... C07C 19/08
[52] U.S. Cl. ............................................................ 570/176
[58] Field of Search ............................................... 570/176

[56] References Cited

FOREIGN PATENT DOCUMENTS

| | | |
|---|---|---|
| 02265933 A2 | 10/1990 | Japan . |
| 3284638 | 12/1991 | Japan . |
| 90/08753 | 8/1990 | WIPO . |
| WO/08753 | 8/1990 | WIPO . |

*Primary Examiner*—Alan Siegel
*Attorney, Agent, or Firm*—Jay P. Friedenson

[57] ABSTRACT

A process for the preparation of 1,1,2,2,3-pentafluoropropane is provided. In the process of the present invention, 1,3-dichloro-1,1,2,2,3-pentafluoropropane is catalytically reduced, using a platinum group metal supported on alumina, to 1,1,2,2,3-pentafluoropropane.

8 Claims, No Drawings

PROCESS FOR THE PREPARATION OF 1,1,2,2,3-PENTAFLUOROPROPANE

This application is a continuation of application Ser. No. 08/418,318 filed Apr. 7, 1995 now abandoned.

FIELD OF THE INVENTION

The present invention relates to a process for the preparation of 1,1,2,2,3-pentafluoropropane, HFC-245ca. In particular, the present invention provides a method for preparing HFC-245ca by the catalytic reduction of 1,3-dichloro-1,1,2,2,3-pentafluoropropane using a platinum group metal supported on alumina.

BACKGROUND OF THE INVENTION

Hydrofluorocarbons, HFC's, are of great interest due to their potential to replace ozone-depleting chlorofluorocarbons, CFC's, which are used in a variety of applications, including refrigerants, solvents, foam blowing agents, and aerosol propellants. For example, 1,1,2,2,3-pentafluoropropane, HFC-245ca, has been identified as a potential refrigerant and foam blowing agent in Japanese patent publication No. 02265933.

The art is actively searching for methods to reduce CFC's to HFC's in order to find suitable replacements for ozone-depleting CFC's. For example, WO 90/08753 to Morikawa et al. disclose a reduction process by which hydrogen-containing 2,2-difluoropropanes are produced. In the disclosed process, the reduction is performed using either zinc and a hydrogen forming agent or hydrogen in the presence of a supported metal catalyst. Morikawa et al. broadly disclose a great number of starting materials, one of which is 1,3-dichloro-1,1,2,2,3-pentafluoropropane, which may be used to form any number of HFC's, one of which is 1,1,2,2,3-pentafluoropropane. Morikawa et al. further disclose the equivalency, for purposes of reducing CFC's, of a wide variety of catalysts supported on a number of inert materials, including both alumina and carbon. Among the many catalysts listed are platinum group elements. Morikawa et al., however, provide no recognition of the superiority of certain supported catalysts in CFC reduction reactions.

As another example of catalytic reduction, Japanese publication No. 3284638 discloses the catalytic hydrogenation of haloethanes of the formula $CF_2xCyCl_2$, where x and y may be fluorine or chlorine. The hydrogenation is carried out in the presence of a palladium-iron-silver catalyst to produce HCFC's of the formula $CF_2xCHyCl$.

The present invention provides a method for catalytically reducing HCFC-225cb to EFC-245ca using a supported platinum group metal catalyst. It has been unexpectedly discovered that the process of the present invention provides both an economical method for the production of BFC-245ca and a method that is amenable to large scale manufacture.

DESCRIPTION OF THE INVENTION

The present invention relates to a process for the reductive dechlorination of $CClF_2CF_2CFHCl$, 1,3-dichloro-1,1,2,2,3-pentafluoropropane or HCFC-225cb, to $CHF_2CF_2CFH_2$, 1,1,2,2,3-pentafluoropropane or HFC-245ca. The process comprises the step of contacting the HCFC-225cb and hydrogen in the presence of a catalyst supported on alumina. The catalyst useful in the reduction reaction of the present invention is selected from palladium, platinum, ruthenium, rhodium, iridium, and mixtures thereof and the reaction is carried out under conditions sufficient to produce a product stream of HFC-245ca.

It has been discovered that when reductive dechlorination of HCFC-225cb is carried out in the presence of the catalyst of the present invention, HFC-245ca is produced with very little reduction of the fluorine atoms. This is surprising in view of the fact that the reductive dechlorination of $CF_3CFCl_2$ at temperatures as low as 150° C. primarily results in the defluorinated compound $CF_3CH_3$.

The starting material for the process of the present invention, HCFC-225cb, is commercially available. The catalysts useful in the present invention to catalyze the reduction of HCFC-225cb may take any form. However, powders are not preferred in vapor phase reductions because powders are sufficiently small to be carried through the reactor and may cause large pressure drops. Accordingly, the catalysts of the present invention preferably are shaped. The catalysts may be prepared in any shape and by any known technique such as tableting or extrusion. Exemplary shapes include, without limitation, large chunks, spheres, and pellets.

The catalyst useful in the present invention may be selected from any of the platinum group metals such as palladium, platinum, ruthenium, rhodium, iridium, and mixtures thereof. Preferably the catalyst material is palladium. The catalyst material preferably is supported by the inert supporting material alumina in pellet form. The catalyst material may be deposited on the alumina support in any convenient form such as a halide or oxide of the catalyst material. Typically, the desired halide or oxide salt is impregnated on the support, dried, and then reduced to the metal with hydrogen.

The catalysts useful in the present invention also are commercially available. Loadings of the metal catalyst on the support depend upon the metal selected. Commonly, loadings of 0.5 weight percent to 5 weight percent are employed. Examples include, without limitation, 0.5% palladium on ⅛ in. alumina pellets.

The reduction reaction of the present invention may be carried out in either the liquid or the vapor phase. However, for large scale production, the reaction is conducted preferably in a continuous flow system by passing vapors of HCFC-225cb along with hydrogen over the catalyst. Pressure is not critical. Both subatmospheric pressures and pressures up to about 100 atmospheres may be used, the latter being especially useful in batch operations. Atmospheric pressures are frequently most convenient and, thus, preferred.

Useful temperatures range from about 185° C. to about 260° C., preferably from about 245° C. to about 255° C. These temperature ranges are surprising because defluorination of the feed material $CF_3CFCl_2$ has been observed in the presence of palladium at temperatures as low as 150° C. Thus, one of ordinary skill in the art would have expected defluorination to increase with temperature in the process of the present invention.

Based on reaction stoichiometry, the required ratio of hydrogen to HCFC-225cb ranges from about 3:1 to 6:1 moles hydrogen to moles HCFC-225cb. Preferably, the ratio is from about 4:1 to about 5:1.

Conditions for the reaction vary depending, in part, on the activity of the catalyst, which depends in turn on the type of metal used, the metal's concentration on the support, and the contact or residence time in the reactor. Residence times may be adjusted by changing the reaction temperature, the catalyst volume, and the flow rates of hydrogen and/or organic material to be reduced. Useful contact times range from about 10 seconds to about 25 seconds, preferably about 13 seconds. The resulting HFC-245ca may be separated from the product stream via any known separation or purification method such as distillation.

The invention will be clarified further by a consideration of the following examples which are intended to be purely exemplary.

EXAMPLE 1

The hydrogenator reactor used for this control reaction consisted of a vertical 1.25 in. diameter PYREX® glass tube with electrical heating tape on the outside of the tube. A thermocouple measured the inside tube temperature and the tube was packed with 15 cc of 1% Pd/carbon mixed with 35 cc borosilicate glass helices for a total bed volume of 50 cc. Hydrogen flow rate was maintained at 35 cc/min. and organic material was fed through the top of the reactor using a syringe pump. The flow rate of organics was maintained at 5 cc/hr. Effluent from the reactor was condensed in two −78° C. cold traps. The organic flow was started at an initial temperature of 190° C. and maintained between 190° C.–203° C. for four hours. After a total time of three hours, 14.5 g. organics had been fed through the reactor. The cold traps contained 9.84 g. of material. Analysis of the crude material by gas chromatography ("GC") indicated the presence of $CClF_2CF_2CFHCl$ (94.9%), $CHF_2CF_2CFH_2$ (0.88%) and eight minor by-products for a total percentage of 4.2%.

EXAMPLE 2

The hydrogenator reactor of Example 1 was packed with 50 cc of 0.5% Pd/alumina as ⅛ in. pellets mixed with 100 cc borosilicate glass helices for a total bed volume of 150 cc. Hydrogen flow rate was maintained at 55 cc/min. and organic material was fed through the top of the reactor using a syringe pump. The organics flow rate was maintained at 5 cc/hr. Effluent from the reactor was condensed in two −78° C. cold traps. The organics flow was started at an initial temperature of 256° C. and maintained between 245° C.–260° C. for four hours. After a total time of three hours, 14.3 g. organics had been fed through the reactor. The cold traps contained 7 g. material. GC analysis of the crude material indicated $CHF_2CF_2CFH_2$ (75.1%), $CClF_2CF_2CFHCl$ (0.1%) and five by-products for a total area percentage of 24.8%.

EXAMPLE 3

The catalyst and procedure of Example 2 were utilized except that 13.5 g. organics were fed through the reactor in 5½ hours. Hydrogen and organics flow rates were maintained at 95–100 cc/min. and 5 cc/hr., respectively. The organics flow was started at an initial temperature of 245° C. and the temperature maintained at 245° C. to 256° C. The cold traps contained 7.0 g. material GC analysis of which indicated $CHF_2CF_2CFH_2$ (85.8%), $CClF_2CF_2CFHCl$ (0.02%), and six other byproducts for a total area percentage of 14.4%. GC-mass spectroscopy analysis of the cold trap material indicated that the byproducts were $CF_3CF_2CH_3$, $CClF_2CFHCHF_2$, and $CHF_2CHClCHF_2$.

EXAMPLE 4

HCFC-225cb was reduced using the reactor and procedures of Example 2 except that the catalyst was prepared from 0.5% Pd/alumina mixed with 50 cc glass helices. The organics flow rate was 4 cc/hr. with a hydrogen flow rate of 90±10 cc/min. The temperature was maintained at 190°±3° C. for 144 hours. HFC-245ca in an 87–92% selectivity and greater than 98% conversion of HCFC-225cb resulted. As the data from Example 4, shown on Table I below indicate, the Pd/alumina catalyst is stable for 144 hours towards the reduction of HCFC-225cb to HFC-245ca.

TABLE I

| Time (hr.) | 225 cb % conversion | 245 ca % selectivity |
| --- | --- | --- |
| 24 | >98 | 87 |
| 48 | 99 | 88 |
| 72 | >98 | 86 |
| 96 | >98 | 90 |
| 120 | 99 | 93 |
| 144 | >98 | 92 |

As the examples demonstrate, the catalytic reduction of HCFC-225cb using 1% palladium supported on activated carbon yields only negligible amounts of HFC-245ca. In contrast, and as the examples demonstrate, the process of the present invention provides excellent conversion of HCFC-225cb to HFC-245ca using 0.5% palladium supported on alumina. Additionally, this conversion is achieved with less than 10% defluorination and minimal formation of byproducts.

Other embodiments of the invention will be apparent from a consideration of the specification or practice of the invention disclosed. It is intended that the specification and examples be considered as exemplary with the true scope and spirit of the invention being indicated in the following claims.

What is claimed is:

1. A process for producing 1,1,2,2,3-pentafluoropropane comprising: contacting hydrogen and 1,3-dichloro-1,1,2,2,3-pentafluoropropane over a catalyst supported on alumina, the catalyst selected from the group consisting of palladium, platinum, ruthenium, rhodium, iridium, and mixtures thereof, under reaction conditions sufficient to produce 1,1,2,2,3-pentafluoropropane.

2. The process of claim 1 wherein the contacting step is conducted in the vapor phase.

3. The process of claim 2 wherein the catalyst is palladium.

4. The process of claim 1 wherein the conditions include temperatures from about 185° C. to about 260° C.

5. The process of claim 4 wherein the conditions include contact times from about 10 seconds to about 25 seconds.

6. The process of claim 5 wherein the mole ratio of hydrogen to 1,3-dichloro-1,1,2,2,3-pentafluoropropane is from about 3:1 to about 6:1.

7. A process for producing 1,1,2,2,3-pentafluoropropane comprising: contacting hydrogen and 1,3-dichloro-1,1,2,2,3-pentafluoropropane, in a mole ratio of hydrogen to 1,3-dichloro-1,1,2,2,3-pentafluoropropane of from about 4:1 to about 5:1, over a palladium catalyst supported on alumina at a temperature from about 245° C. to about 255° C. for a contact time of about 13 seconds.

8. A process for producing 1,1,2,2,3-pentafluoropropane comprising: contacting hydrogen and 1,3-dichloro-1,1,2,2,3-pentafluoropropane over a palladium-catalyst supported on alumina under reaction conditions sufficient to produce 1,1,2,2,3-pentafluoropropane.

* * * * *

UNITED STATES PATENT AND TRADEMARK OFFICE
CERTIFICATE OF CORRECTION

PATENT NO : 5,856,594
DATED : January 5, 1999
INVENTOR(S) : Thenappan et al.

It is certified that error appears in the above-identified patent and that said Letters Patent are hereby corrected as shown below:

Column 1, line 51, delete "EFC" and substitute therefor -- HFC --.

Column 1, line 54, delete "BFC" and substitute therefor -- HFC --.

Signed and Sealed this

Eighth Day of May, 2001

Attest:

NICHOLAS P. GODICI

Attesting Officer

Acting Director of the United States Patent and Trademark Office